US006773722B2

(12) United States Patent
Zagnoli et al.

(10) Patent No.: US 6,773,722 B2
(45) Date of Patent: Aug. 10, 2004

(54) PROCESS FOR THE PREPARATION OF GRANULAR AND POROUS SUCRALFATE DRY GEL

(75) Inventors: Giorgio Zagnoli, Como (IT); Paolo Colombo, Parma (IT); Loretta Maggi, San Giorgio Piacentino (IT); Fabrizio Cudazzo, Lecce (IT)

(73) Assignee: Laboratorio Italiano Biochimico Farmaceutico Lisapharma S.p.A., Como (IT)

( * ) Notice: Subject to any disclaimer, the term of this patent is extended or adjusted under 35 U.S.C. 154(b) by 0 days.

(21) Appl. No.: 10/449,266

(22) Filed: May 29, 2003

(65) Prior Publication Data

US 2003/0206950 A1 Nov. 6, 2003

Related U.S. Application Data

(62) Division of application No. 09/744,869, filed as application No. PCT/EP99/03879 on Jun. 4, 1999.

(30) Foreign Application Priority Data

Jul. 30, 1998 (IT) .......................................... MI98A1785

(51) Int. Cl.[7] ................................................. A61K 9/28

(52) U.S. Cl. ....................................... 424/474; 424/464
(58) Field of Search ................................. 424/464, 465, 424/474, 400, 489, 451

(56) References Cited

FOREIGN PATENT DOCUMENTS

WO          WO 9605843 A1  *  2/1996  .......... A61K/31/70

* cited by examiner

Primary Examiner—Gollamudi S. Kishore
Assistant Examiner—Robert M. Joynes
(74) Attorney, Agent, or Firm—Abelman, Frayne & Schwab

(57) ABSTRACT

Sucralfate gel in the dry state in porous granular form having a particle-size distribution of between 100 and 1000 µm, an apparent density of the powder bed of between 0.7 and 0.9 g/ml, a settling index of between 5 and 15%, and a residual humidity of between 5 and 15%, and the corresponding process of preparation, which comprises a treatment with microwaves of a diluted solution of powdered sucralfate gel, with a sucralfate titer of between 20 and 70 wt. %. This solid product may be advantageously used in the preparation of solid pharmaceutical compositions that contain it as single active principle, or else as coating of solid compositions that contain, as active principle, a substance that may cause lesions to the gastric mucosa.

4 Claims, 3 Drawing Sheets

PROCESS FOR THE PREPARATION OF GRANULAR AND POROUS SUCRALFATE DRY GEL

This application is a division of Ser. No. 09/744,869 filed Jan. 29, 2001, which is a 371 of PCT/EP99/03879 filed Jun. 4, 1999.

SCOPE OF INVENTION

The present invention regards a solid form of dry sucralfate gel in porous granular form, the process for its preparation, and pharmaceutical compositions that contain it either as active principle, or for pharmaceutical compositions comprising it as coating and other active principles that may cause lesions to the gastric mucosa.

STATE OF THE ART

Sucralfate is a drug for the treatment of ulcers for which a non-systemic mechanism of action has been proposed. In fact, its activity depends upon its capacity to bind to the ulcerated sites of the gastric mucosa, thus creating a physical barrier that is able to protect the mucosa from the aggression of acids and enzymes. This mechanism has stimulated pharmaceutical research workers to improve those characteristics of the product that have a direct influence on its capacity to exert an action of "protective coating" of the gastro-intestinal wall. Particular attention has been directed to the granulometric characteristics and the specific surface area of the preparation, to its physical structure (crystallinity, structure of bound water, etc.) and to its reactivity with acids. Recently, this "classic" mechanism of action has been enhanced by new experimental findings, which, without taking anything away from the need for sucralfate to interact with the gastro-intestinal mucosa, have shown that also mechanisms linked to the activity of the $PGE_2$ prostaglandins or of the Epidermal Growth Factor must be taken into account. More recently, significant light has been shed on the role that a micro-organism, *Helicobacter pylori*, plays in the development of pathological conditions involving gastric erosion. Many research workers are convinced that the reason for which the bacterium manages to settle in an environment which is decidedly hostile on account of the high gastric acidity, is to be sought in the capacity of the said bacterium to attach to the epithelial cells of the stomach, which are able to offer various binding sites. It may be inferred from this how important it is to be able to prevent the implantation of the bacterium by identifying a therapeutic means that is able to compete with the bacterium for the binding sites or to attack it with a specific action, such as localized antibiotic treatment. To achieve this, a therapeutic tool is needed that can bind to the mucosa, compete with the binding sites of the germ, and convey and keep in situ an antibacterial agent to which the germ is sensitive.

The European Patent EP 0286978 describes a physical form of sucralfate, referred to as "gel" on account of its peculiar colloidal characteristics. Sucralfate gel could take on the role of agent expressly designed to counteract *Helicobacter pylon* and its harmful consequences. In fact, this new gel form of sucralfate has proved to possess impressive bio-adhesive characteristics in regard to the gastric mucosa, its adhesive property being much higher than the one possessed by sucralfate in the powder form. This biophysical superiority has determined a higher anti-!ulcer activity, so much so that the sucralfate gel form has made it possible to halve the therapeutic dose of sucralfate from 4 g/day to 2 g/day, with unquestionable advantages, also in terms of patient compliance.

From the technological point of view, this superior activity of sucralfate gel has been obtained thanks to an original process of production of the starting material. The active principle sucralfate is a complex salt of sucrose octasulphate with aluminium hydroxide, and the manufacturing process concludes with the precipitation of the salt from an aqueous solution of the two counter-ions, aluminium and sucrose octasulphate, with a subsequent drying phase that gives rise to an amorphous powder.

The innovation obtained with sucralfate gel is represented by the change in the physical properties, so as to obtain a colloidal form. This physical colloidal form, referred to as "gel", is demonstrated not only by the granulometric properties, but above all by the thixotropic rheological characteristics of the aqueous suspension of sucralfate gel, which account for its high capacities of adhesion to the mucosae of the gastro-intestinal tract.

The rheological and bio-adhesive properties of sucralfate gel are lost when the precipitated gel is brought to the dry state by means of ordinary techniques of drying using heat or vacuum-drying. Consequently, the starting material sucralfate gel used for the preparation of the pharmaceutical forms consists of a moist solid that is simply the filtered precipitate containing a large quantity of water bound to the colloidal particles of sucralfate. Keeping the starting material in the dry state is a necessary condition and the only way for preserving the superior activity of sucralfate gel. This means that the pharmaceutical forms that can be prepared with the moist solid are only the aqueous suspensions.

This fact, however, poses strict limits on the pharmaceutical forms available for the therapy using sucralfate gel, in so far as it does not enable the preparation of solid pharmaceutical forms, such as tablets, capsules, tablets for chewing or powder. In fact, the current form of administration of sucralfate gel is necessarily an aqueous suspension which, even though it may be very suitable for the type of pathological condition and for the role that the product must perform, raises problems linked to the high volumes to be transported, possibilities of bacterial pollution, and impracticality of use.

The international patent application WO9605483 presents a spray-drying process for sucralfate gel developed starting from an aqueous suspension of sucralfate gel, in which an appropriate amount of a gel-protective agent was present, i.e., a compound provided with hydroxyl groups. The solid compound obtained from this drying technique, when re-dispersed in water, gave rise to a suspension that possessed the same characteristics as those of the starting products; namely, it presented gel properties.

Unfortunately, this method for drying sucralfate gel proved somewhat disadvantageous, in that it involved a long and laborious process that entailed mixing of mannitol in considerable quantities with sucralfate gel, long drying times with considerable expenditure of energy, and yields of around 50%. In addition, the spray-dried product obtained, which had dimensions of just a few micron, had to undergo further stages of treatment in order to arrive at a granulate suitable for the preparation of pharmaceutical forms, such as ordinary tablets of tablets for chewing.

SUMMARY OF INVENTION

Now we have found, and this constitutes the main subject of the present invention, a new form of granular and porous dry sucralfate gel, which is particularly suitable for the preparation of solid pharmaceutical forms that are able to preserve, once re-dispersed in water, the peculiar properties of a gel.

This sucralfate gel in solid form presents a particle-size distribution of between 100 and 1000 μm, an apparent density of the powder bed of between 0.7 and 0.9 g/ml, a settling index, as defined by R. L. Carr in "Evaluating flow properties of solids", Chem. Eng. 72:163–168 (1965), of between 5 and 15%, and, finally, a residual humidity of between 5 and 15%.

A further subject of the present invention is the process of preparation of the above-mentioned solid form, which comprises the following steps:
- a) A diluted aqueous dispersion is prepared, which presents a viscosity of between 10 and 20 mPa.s, of powdered sucralfate gel.
- b) The diluted aqueous suspension obtained from step (a) is subjected to drying by treatment with microwaves.

This drying technique using microwaves makes it possible to overcome the numerous drawbacks linked to the spray-drying process described previously. Unlike the powdered sucralfate gel obtained using the spray-drying techniques, which is characterized by a very fine powder, the powdered sucralfate gel according to the present invention takes the form of a granular and porous solid product which, when brought into contact with water and simply stirred, gives rise to a homogenous suspension of sucralfate gel having the same thixotropic and bio-adhesive properties as the suspension of moist sucralfate gel. Furthermore, it is not necessary to add a gel-protective agent since, in the granular and porous dry sucralfate gel according to the present invention, the typical properties of moist sucralfate gel are maintained without the addition of the said substances in the drying phase, an operation which is instead indispensable in the case of sucralfate gel obtained by means of spray-drying.

Consequently, the dry sucralfate gel in the porous granular form, which is the subject of the present invention, when re-dispersed in water, gives rise to a suspension that possesses the same characteristics as those of the starting suspension; namely, it presents gel properties.

A further subject of the present invention is represented by pharmaceutical compositions in solid form for oral use containing as active principle the dry sucralfate gel in granular and porous form that is the subject of the present invention. The fact that the sucralfate gel according to the present invention comes in the form of an extremely porous granulate makes it particularly useful for conveniently preparing solid pharmaceutical forms, such as tablets that can be chewed, which re-disperse with surprising rapidity in an aqueous means, such as saliva.

A further subject of the present invention is represented by pharmaceutical compositions for oral use comprising:
- i) a core containing an active principle which may cause lesions to the gastric mucosa;
- ii) a coating of the said core which contains as main component the porous granular dry sucralfate gel that is the subject of the present invention.

DETAILED DESCRIPTION OF INVENTION

Figure 1:
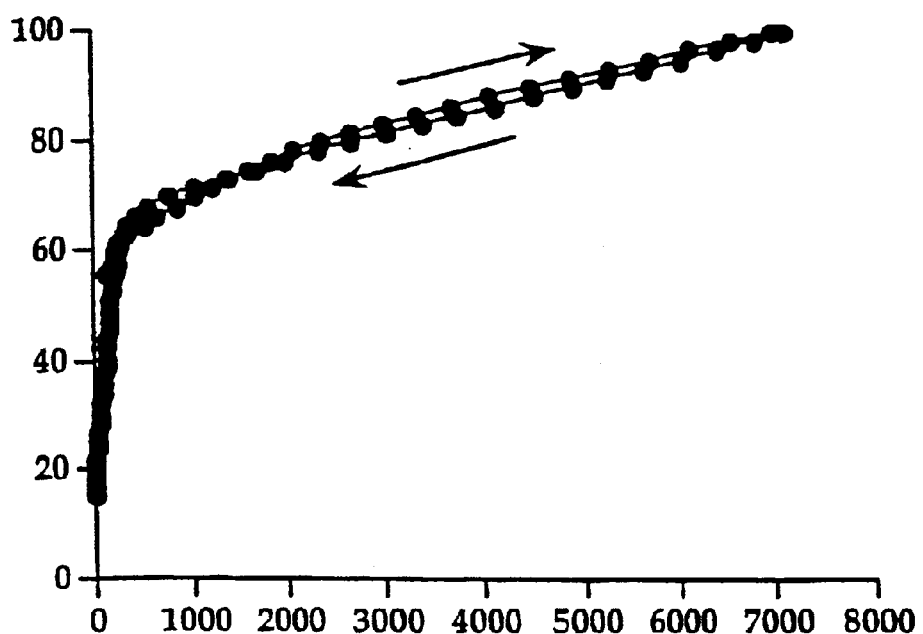
FIG. 1 presents the rheogram for the 20% (w/v) sucralfate gel aqueous suspension before drying, where the viscous shear strength, expressed in Pa, is given on the ordinate, and the shear rate, expressed in $s^{-1}$, is given on the abscissa.
Figure 2:
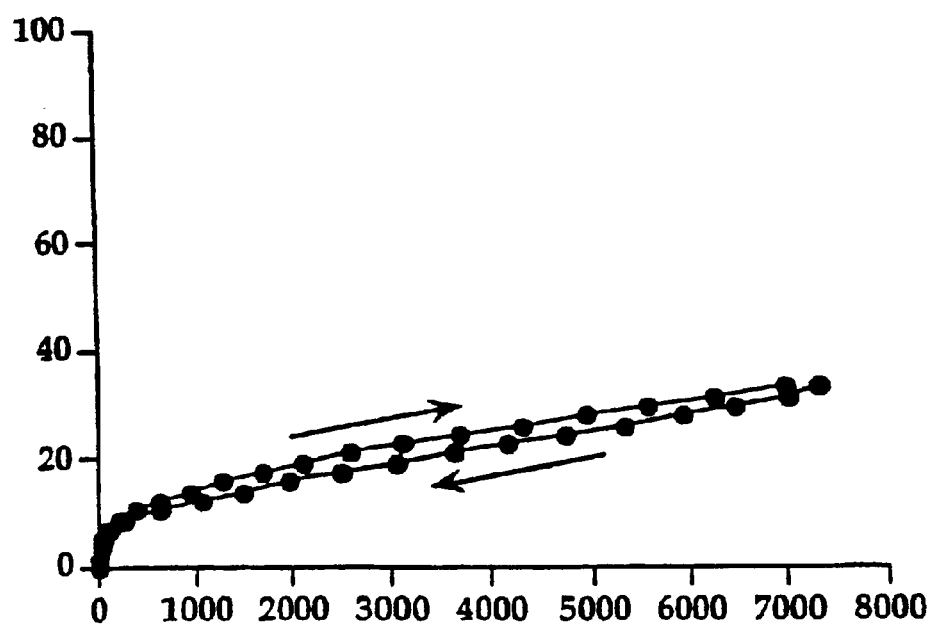
FIG. 2 presents the rheogram for the 20% (w/v) sucralfate gel suspension obtained from spray-drying, where the viscous shear strength, expressed in Pa, is given on the ordinate, and the shear rate, expressed in $s^{-1}$, is given on the abscissa.

In FIGS. 1, 2, 3, 4 and 5, a comparison is made between the rheogram of the suspension of sucralfate gel that has not undergone drying treatment, the rheogram of the sucralfate gel according to the present invention obtained by microwave drying, and the rheogram of the product obtained by means of spray-drying. These rheograms show that the dry sucralfate gel in porous granular form according to the present invention makes it possible to preserve the rheological characteristics of moist sucralfate gel. In practice, the rheological and bio-adhesive characteristics, as well as the particle-size distribution of the particles of the reconstituted suspension do not appear changed with respect to the starting product prepared with moist sucralfate gel. As a consequence of this, the dry product is defined as dry sucralfate gel in porous granular form.

The process of preparation of the above-mentioned dry sucralfate gel, which is a further subject of the present invention and involves the use of microwaves for drying, i.e., step (b), has surprisingly shown considerable advantages with respect to the spray-drying process, and in particular:
- the drying of moist sucralfate gel may occur directly without any addition of substances provided with hydroxyl groups that have a "gel-protective" function, such as mannitol;
- the drying operation requires decidedly shorter times with respect to the spray-drying process;
- the yields obtained by means of the present process are around 100%, whereas with spray-drying, they do not go beyond 50%.

The moist sucralfate gel in powder form used in step (a) of the process according to the present invention is prepared as described in the above-mentioned European Patent EP 0286978 and presents a sucralfate titre (as emerges from the Italian Pharmacopoeia) of between 20 and 70 wt %.

Preferably used as sucralfate gel is the one presenting a sucralfate titre of between 30 and 50 wt %.

The sucralfate concentration in the aqueous dispersion, expressed as weight of sucralfate contained in the starting sucralfate gel over the total volume of the said dispersion, in step (a) of the process which is the subject of the present invention is preferably of between 10 and 25%.

As previously emphasized, the solid product obtained with this process takes the form of an extremely porous granulate. The product presents a high density and considerable properties of cohesion without the aid of binding agents, thus making it possible to prepare easily solid pharmaceutical forms, such as chewable tablets, without any granulation treatment prior to the compression operation. In particular, the innovative characteristics of this new quality of dry sucralfate gel are the particle size and the apparent density of the powder, as well as the porosity of the granules obtained using the microwave drying process. The average size of the sucralfate gel powder obtained is 500 μm for the dry sucralfate gel according to the present invention employing microwaves, and 10 μm for the dry sucralfate gel obtained by spray-drying. The apparent density of the powder bed in settled conditions has proved to be, for the dry sucralfate gel according to the present invention, between 0.7 and 0.9 g/ml, and, for spray-dried sucralfate gel, between 0.4 and 0.6 g/ml. The settling index of the powder bed, i.e., the percentage increase in density of the powder bed as a result of a settling action applied to the bed itself, has been found to be between 5 and 15% for the sucralfate gel dried using microwaves, and between 30 and 50% for the sucralfate gel dried using the spray-drying technique.

Residual humidity in the dry sucralfate gel in porous granular form according to the present invention is between 5 and 15%, whilst the corresponding value for the sucralfate gel dried using the spray-drying technique does not exceed 4%.

Even though, as has been pointed out previously, the porous dry sucralfate gel according to the present invention does not require the presence of a gel-protective agent in the preparation phase via drying, it contains a gel-protective agent even so, in quantities, expressed as weight of sucralfate contained in the sucralfate gel with respect to the weight of the gel-protective agent, of between 0.5:1 and 1.5:1.

The gel-protective agent is preferably chosen from among: mannitol, sorbitol, glucose, sucrose, lactose, xylitol, and polyalcohols.

This new form of dry sucralfate gel according to the present invention was discovered unexpectedly when a diluted suspension of sucralfate was subjected to drying. The fact that all this was unforeseeable is linked to the circumstance that the consolidated technique teaches that it is more advantageous to dry a product in which the quantity of water present is as low as possible. Instead, we discovered that drying a more diluted suspension of sucralfate gel, using the microwave technique, causes boiling of the product which leads to the formation of a high number of empty spaces in the desiccate. In particular, it has been found that this boiling phenomenon is linked to the viscosity of the aqueous suspension that is to undergo microwave treatment, a viscosity which, as has been pointed out above, must be of between 10 and 20 mPa.s. Even more surprisingly, it has been discovered that the porosity of the dry product obtained from this process is able to activate the disgregation of the tablets, which in practice are demolished into the original particles without the intervention of disgregating substances, as instead currently is the case in the technology of pharmaceutical tablets. In fact, the tablets obtained starting from dry sucralfate gel according to the present invention, when put in water, manifest the unusual tendency to disgregate by themselves by virtue of the high porosity of the starting material.

The dry sucralfate gel which is the subject of the present invention presents superior qualities of compression and cohesion as compared to the known forms of sucralfate whether in powder form or in dry gel form. This means that the dry sucralfate gel according to the present invention may be used in making tablets or the like, even in those production situations in which sucralfate is used in particular technologies, such as those employed to create a barrier aimed at providing an outer coating for a dry-coated tablet. This technology is described in the European Patent No. 0167958 and consists in the application, to a core, preferably in the form of a tablet containing a drug with properties that are harmful for the stomach wall, of a coating containing, as main component, sucralfate, which has the function of protecting the gastric mucosa before this comes into contact with the gastrolesive drug that is harmful for the stomach. In this coating technology certain aspects are of primary importance for the production and operation of the therapeutic preparation: the amount of coating must be as limited as possible; the properties of cohesion of the coating must be high; and the disgregation of the coating, which precedes disgregation of the core, must be obtained rapidly, with as little intervention as possible of auxiliary substances, such as disgregating agents. The use of dry sucralfate gel in granular and porous form according to the present invention is able to meet fully all the above requirements, in that the product has twice the activity of sucralfate in powder form, and hence the quantity applied for the coating is halved. The granular form favours the cohesion both between the particles forming the coating and between the coating and the core, thus overcoming the drawbacks of poor gloss and hardness of the coating and of detachment of the coating from the core in the phases of packaging of the finished product. The porosity of the granulate leads to an independent disgregation of the coating, even without the use of disgregating agents.

For this reason, there forms a subject of the present patent also the use of dry sucralfate gel according to the present invention in the preparation of dry-coated tablets, in which the outer layer consists of sucralfate, and the core consists of an agent that may cause lesions to the stomach, such as aspirin, ibuprofen, ketoprofen, diclofenac, piroxicam, and nimesulide. In fact, in this case, the use of sucralfate gel, which possesses twice the activity of that of powdered sucralfate used in the European patent quoted previously, makes it possible to reduce by half the quantity of sucralfate necessary for the therapeutic activity of protection of the gastric mucosa from contact with the anti-inflammatory agent contained in the core. However, of particular importance is the fact that, for the high characteristics of compression and cohesion, the dry sucralfate gel according to the present invention enables a superior quality of the prepared tablet to be obtained, both as regards the simplification of the process of production and as regards the cohesion between the layer of coating and the core. With the dry sucralfate gel in granular and porous form according to the present invention, it is easier to prepare solid pharmaceutical compositions for oral administration, for the reason that it is already in a granular form, and not in a microgranular form, and thus enables a greater rapidity of disgregation on account of its extreme porosity.

In order to provide some illustrations of the present invention, which, however, do not have any limiting effect, hereinafter a number of examples are given of preparations of porous dry sucralfate gel and of pharmaceutical compositions in a solid form which contain the porous dry sucralfate gel according to the present invention either as active principle or as outer coating of pharmaceutical compositions of an active principle that may cause lesions to the gastric mucosa.

EXAMPLE 1.1

Preparation of Dry Sucralfate Gel by Means of Microwave Drying

| | |
|---|---|
| Moist sucralfate gel | 100 g (containing 30.8 g of sucralfate, Italian Official Pharmacopoeia) |
| Depurated water q.s. up to | 200 ml |

The mixture of components is agitated in a turbine mixer to obtain a fine dispersion of the sucralfate gel. The suspension obtained in a quantity of 200 ml is put in a microwave oven having a volume of 17 lit., spread in a dish having a diameter of 27.5 cm, so that the thickness of the layer may be approximately 4 mm., and subjected to microwave radiation, at a power of 800 W and an intermittence of 24–30 sec., for a total time of 20 minutes. In the conditions described above, 30 g of dried product are obtained which presents a value of residual humidity of between 10 and 15%.

Figure 3:
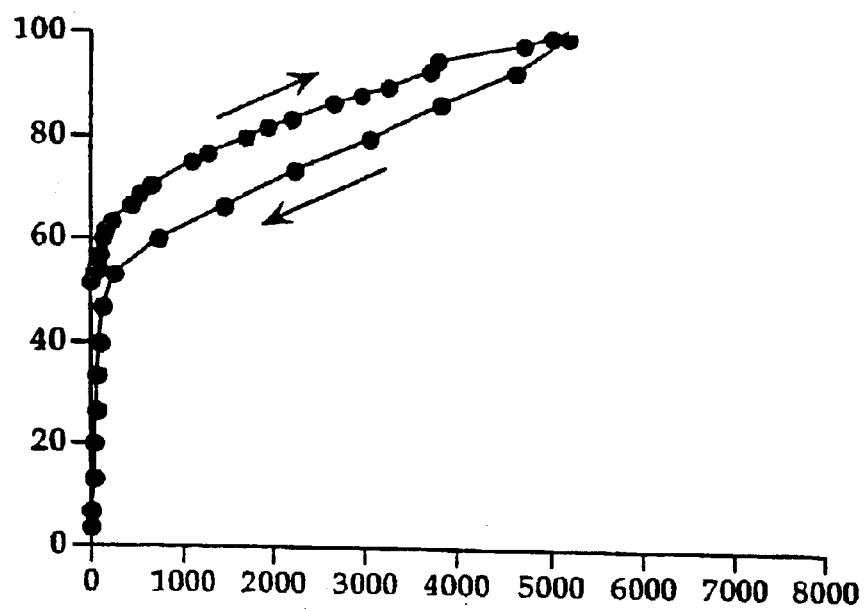
FIG. 3 presents the rheogram for the 20% (w/v) porous granular dry sucralfate gel suspension according to the present invention, where the shear strength, expressed in Pa, is given on the ordinate, and the shear rate, expressed in $s^{-1}$, is given on the abscissa.

The dispersion in depurated water of 30 g of dried product, by mixing in a turbine mixer, in order to obtain a 20% (w/v) sucralfate gel, presents rheological characteristics similar to the ones that the sucralfate gel possessed before drying. FIG. 1 shows the rheogram of the suspension of moist sucralfate gel before drying, taken as a reference in the comparison with the rheogram of the suspension containing moist sucralfate gel dried using the spray-drying technique (FIG. 2) and with the rheogram of the suspension containing moist sucralfate gel dried using the microwave technique (FIG. 3).

EXAMPLE 1.2
Preparation of Dry Sucralfate Gel Containing Mannitol in a 1:1 Ratio, by means of Microwave Drying

| Moist sucralfate gel | 100 g (containing 42 g of sucralfate, Italian Official Pharmacopoeia) |
|---|---|
| Mannitol | 42 g |
| Depurated water q.s. up to | 250 ml |

The mixture of components is agitated in a turbine mixer to obtain a fine dispersion of the sucralfate gel. The suspension obtained is dried in the same operating conditions as those of the previous example. Approximately 80 g of dried product are obtained which presents a value of residual humidity of between 10 and 15%.

The dispersion in depurated water of 30 g of dried product, simply by mixing, in order to obtain a 20% (w/v) dry sucralfate gel, presents rheological characteristics similar to the ones that the sucralfate gel possessed before drying.

EXAMPLE 1.3
Preparation of Dry Sucralfate Gel Containing Mannitol in a 1:1.5 Ratio, by Means of Microwave Drying

| Moist sucralfate gel | 100 g (containing 30.8 g of sucralfate, Italian Official Pharmacopoeia) |
|---|---|
| Mannitol | 46.2 g |
| Depurated water q.s. up to | 200 ml |

Figure 4:
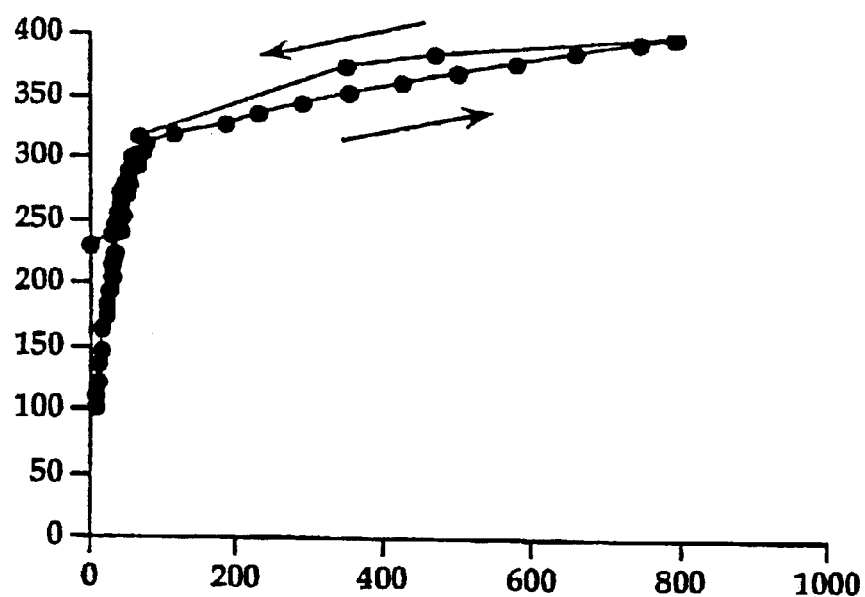
FIG. 4 presents the rheogram for the 20% (w/v) sucralfate gel aqueous suspension containing mannitol present in an amount expressed as weight of mannitol with respect to weight of sucralfate in the sucralfate gel of 1.5:1 before drying, where the shear strength, expressed in Pa, is given on the ordinate, and the shear rate, expressed in $s^{-1}$ is given on the abscissa.
Figure 5:
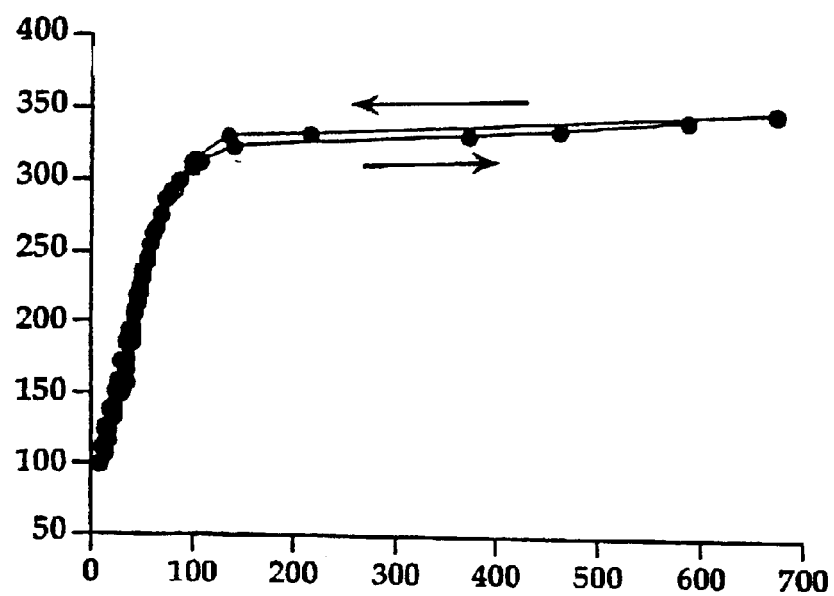
FIG. 5 presents the rheogram for the 20% (w/v) sucralfate gel aqueous suspension containing mannitol present in an amount expressed as weight of mannitol with respect to weight of sucralfate in the sucralfate gel of 1.5:1, where the shear strength, expressed in Pa, is given on the ordinate, and the shear rate, expressed in $s^{-1}$, is given on the abscissa.

The mixture of components is agitated using a turbine mixer to obtain a fine dispersion of the sucralfate gel. The suspension obtained is dried in the same operating conditions as those of the previous example. Approximately 70 g of dried product are obtained which presents a value of residual humidity of 4.7%. The dispersion in depurated water of 30 g of dried product thus obtained, simply by mixing, in order to obtain a 20% (w/v) dried sucralfate gel, presents rheological characteristics similar to the ones that the sucralfate gel possessed before drying. FIG. 4 presents the rheogram for the suspension of moist sucralfate gel containing mannitol in the ratio of 1:1.5, before drying, taken as reference for the comparison with the rheogram for the suspension containing moist sucralfate gel containing the same proportion of mannitol, dried using the microwave technique (FIG. 5).

EXAMPLE 2.1
Preparation of Chewable Tablets of Sucralfate Gel Dried Using the Microwave Technique, Containing Mannitol in a 1:1 Ratio
Composition of a Tablet Weighing 2.438 g

| Sucralfate, as dry gel | 1 g |
|---|---|
| Mannitol | 1 g |
| Aspartame | 0.0014 g |
| Mint essence | 0.004 g |
| Liquorice essence | 0.004 g |
| Magnesium stearate | 0.024 g |

Sucralfate gel dried by means of the microwave technique, containing mannitol in a 1:1 ratio with respect to the sucralfate was obtained following the operating conditions of Example 1.2. To obtain the tablets, the dry sucralfate gel was sieved through a 1-mm mesh sieve. Mint and liquorice flavouring, aspartame and magnesium stearate were then added to the granulate, and the mixture was put in a rotating-body mixer for 1 hour. Tablets were produced from this mixture, using a layer press provided with 20-mm diameter punches.

The tablets obtained presented an average weight of 2.43±0.02 g, a thickness of 6.04±0.01 mm, a friability of 1.45%, a Monsanto hardness of 5.2±0.3, and a disgregation time, according to the Italian Official Pharmacopoeia, of 6±2 min.

EXAMPLE 2.2
Aspirin Tablets (100 mg) Coated with 100 mg of Dry Sucralfate Gel Dried Using the Microwave Technique
Composition of a Tablet Weighing 249.1 mg:

| Core | |
|---|---|
| acetylsalicylic acid | 100 mg |
| maize starch | 10 mg |
| croscaramellose | 3 mg |
| Coating | |
| sucralfate, as dry gel | 100 mg |
| croscaramellose | 4.7 mg |
| magnesium stearate | 1.2 mg |

For the preparation of the core, starch and croscaramellose were added to the acetylsalicylic acid, and these were mixed together in a rotating-body mixer for one hour. The tablets were prepared using a layer press equipped with rounded punches having a diameter of 6 mm.

The dry sucralfate gel for the preparation of the coating was obtained according to Example 1.1. The dry sucralfate gel, which was sieved through a sieve with a 1-mm mesh, was mixed with croscaramellose and magnesium stearate in a rotating-body mixer for one hour. The acetylsalicylic acid tablets were coated with this mixture using a layer press equipped with rounded punches having a diameter of 9 mm. The tablets obtained presented an average weight of 258±7 mg, a thickness of 3.8±0.04 mm, a friability of 0.6%, a Monsanto hardness of 4.2±0.7, and a disgregation time, according to the Italian Official Pharmacopoeia, of 3.5±2 min.

What is claimed is:

1. A pharmaceutical dry-coated tablet for oral use, which comprises:
   a. a core containing an active principle which may cause lesions to the gastric mucosa as a side effect; and
   b. a coating of said core which contains as the main component dry sucralfate gel in granular and porous solid form in which the granules present a particle size distribution of between 100 and 1000 μm, an apparent density of the powder of between 0.7 and 0.9 g/ml, and a settling index of between 5 and 15%.

2. The pharmaceutical dry-coated tablet according to claim 1, wherein the active principle that may cause lesions to the gastric mucosa is selected from the group consisting of acetylsalicyclic acid, ibuprofen, ketoprofen, diclofenac, piroxicam and nimesulide.

3. The pharmaceutical dry-coated tablet according to claim 1, wherein dry sucralfate gel in granular and porous solid form contains a gel-protective agent, in quantities expressed as weight of sucralfate contained in sucralfate gel with respect to weight of gel-protective agent, of between 0.5:1 and 1.5:1.

4. The pharmaceutical dry-coated tablet in granular and porous solid form according to claim 2, wherein said gel-protective agent is selected from the group consisting of mannitol, sorbitol, glucose, sucrose, lactose, xylitol and polyalcohols.

* * * * *